(12) United States Patent
Sarkela et al.

(10) Patent No.: US 9,072,482 B2
(45) Date of Patent: *Jul. 7, 2015

(54) METHOD AND APPARATUS FOR AUTOMATIC SEIZURE MONITORING

(75) Inventors: Mika Sarkela, Espoo (FI); Antti Tolonen, Tampere (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 482 days.

This patent is subject to a terminal disclaimer.

(21) Appl. No.: 12/883,286

(22) Filed: Sep. 16, 2010

(65) Prior Publication Data
US 2012/0071779 A1   Mar. 22, 2012

(51) Int. Cl.
*A61B 5/04* (2006.01)
*A61B 5/00* (2006.01)
*A61B 5/048* (2006.01)

(52) U.S. Cl.
CPC ............. *A61B 5/4094* (2013.01); *A61B 5/7264* (2013.01); *A61B 5/7275* (2013.01); *A61B 5/04008* (2013.01); *A61B 5/048* (2013.01)

(58) Field of Classification Search
CPC ........ A61B 5/0476; A61B 5/048; A61B 5/72; A61B 5/7235–5/7267
See application file for complete search history.

(56) References Cited

U.S. PATENT DOCUMENTS

| | | | |
|---|---|---|---|
| 5,241,967 A * | 9/1993 | Yasushi et al. | 600/545 |
| 6,658,287 B1 * | 12/2003 | Litt et al. | 600/544 |
| 7,461,045 B1 * | 12/2008 | Chaovalitwongse et al. | 706/52 |
| 8,600,493 B2 * | 12/2013 | Tanner et al. | 600/544 |
| 2002/0103512 A1 * | 8/2002 | Echauz et al. | 607/9 |
| 2004/0127810 A1 * | 7/2004 | Sackellares et al. | 600/544 |
| 2004/0243328 A1 * | 12/2004 | Rapp et al. | 702/71 |
| 2007/0055169 A1 * | 3/2007 | Lee et al. | 600/544 |
| 2007/0213786 A1 * | 9/2007 | Sackellares et al. | 607/45 |
| 2007/0249956 A1 * | 10/2007 | Carlson et al. | 600/544 |
| 2009/0124923 A1 * | 5/2009 | Sackellares et al. | 600/544 |

OTHER PUBLICATIONS

Ataee, P., Yazdani, A., Setarehdan, S. & Noubari, H. A. Manifold learning applied on EEG signal of the epileptic patients for detection of normal and pre-seizure States. Conference of the IEEE Engineering in Medicine and Biology Society 2007, 5489-5492 (2007).*

Babloyantz, A. & Destexhe, A. Low-Dimensional Chaos in an Instance of Epilepsy. Proceedings of the National Academy of Sciences 83, 3513-3517 (1986).*

(Continued)

*Primary Examiner* — Soren Harward

(57) ABSTRACT

Method, apparatus and computer program product for monitoring seizure activity in brain are disclosed. At least one parameter set sequence is derived from brain wave signal data obtained from a subject, wherein each parameter set sequence comprises sequential parameter sets and each parameter set comprises values for at least two signal parameters, the values being derived from the brain wave signal data. A path formed by each of the at least one parameter set sequence in a parameter space is determined, thereby to obtain at least one path. The parameter space is defined by the at least two signal parameters. At least one evolution indicator is calculated, each evolution indicator quantifying the evolution occurred in respective path formed in a given time period in the parameter space. The at least one evolution indicator is then employed to produce an indication of seizure activity in the brain wave signal data.

14 Claims, 5 Drawing Sheets

(56) References Cited

OTHER PUBLICATIONS

Gabor, A. J., Leach, R. R. & Dowla, F. U. Automated seizure detection using a self-organizing neural network. Electroencephalography and Clinical Neurophysiology 99, 257-266 (1996).*

Hegde, A., Erdogmus, D., Rao, Y. N., Principe, J. C. & Gao, J. SOM-based similarity index measure: quantifying interactions between multivariate structures. Workshop on Neural Networks for Signal Processing 819-828 (2003).*

Joutsiniemi, S.-L., Kaski, S. & Larsen, T. A. Self-organizing map in recognition of topographic patterns of EEG spectra. IEEE Transactions on Biomedical Engineering 42, 1062-1068 (1995).*

Tambouratzis, G., Papakonstantinou, G., Stamatelopoulos, S., Zakopoulos, N. & Moulopoulos, S. Analyzing the 24-hour blood presure and heart-rate variability with self-organization feature maps. International Journal of Intelligent Systems 17, 63 (2002).*

Aarabi, A., Wallois, F. & Grebe, R. Automated neonatal seizure detection: a multistage classification system through feature selection based on relevance and redundancy analysis. Clin. Neurophysiol. 117, 328-340 (2006).*

Greene, B. R. et al. A comparison of quantitative EEG features for neonatal seizure detection. Clin. Neurophysiol. 119, 1248-1261 (2008).*

Carter, B. Filter Design in Thirty Seconds. (2001).*

Lopour, B. A., Tasoglu, S., Kirsch, H. E., Sleigh, J. W. & Szeri, A. J. A continuous mapping of sleep states through association of EEG with a mesoscale cortical model. Journal of Computational Neuroscience 30, 471-487 (2011).*

Pardalos, P. M. et al. Analysis of EEG data using optimization, statistics, and dynamical system techniques. Computational Statistics & Data Analysis 44, 391-408 (2003).*

Raiesdana, S., Golpayegani, S. M. R. H., Firoozabadi, S. M. P. & Mehvari Habibabadi, J. On the discrimination of patho physiological states in epilepsy by means of dynamical measures. Computers in Biology and Medicine 39, 1073-1082 (2009).*

Young et al, "An assessment of noncolvusive seizures in the intensive care unit using continuous EEG monitoring: An investigation of variables associated with mortality", Neurology 1996; 47:83-89.

De Clercq et al, "Characterization of interictal and ictal scalp EEG signals wit the Hilbert transform", 25th Annual International Conference of the IEEE EMBS, 2003; 2459-2462.

Hofmann et al, "Unsupervised Classification of EEG from subdural Seizure Recordings", Brain Topography, 10:121-132, 1997.

Acar et al, Seizure Recognition on Epilepsy Feature Tensor, 29th Annual International Conference of the IEEE Engineering in Medicine and Biology Society, 2007.

Wendling et al, "Extraction of Spatio-Temporal Signatures From Depth EEG Seizure Signals Based on Objective Matching in Warped Vectorial Observations", IEEE Transactions on Biomedical Engineering, 43:990-1000, 1996.

Mormann et al, "On the predictability of epileptic seizures", Clinical Neurophysiology, 116:569-587, 2005.

Wu et al, "Segmentation and classification of EEG during epileptic seizures", Electroencephalography and Clinical Neurophysiology, 106:344-356, 1998.

Bao et al, "A New Approach to Automated Epileptic Diagnosis Using EEG and Probabilistic Neural Network", 20th IEEE Conference on Tools with Artificial Intelligence, 2008, vol. 2:482-486.

Gotman "Automatic recognition of epileptic seizures in the EEG", Electroencephalography and Clinical Peurophysiology, 54:530-540, 1982.

Grewal et al, "An automatic warning system for epileptic seizures recorded on intracerebral EEGs", Clinical Neurophysiology, 116:2460-2472, 2005.

Khan et al, "Wavelet based automatic seizure detection in intracerebral electroencephalogram", Clinical Neurophysiology, 114:898-908, 2003.

Saab et al, "A system to detect the onset of epileptic seizures in scalp EEG", Clinical Neurophysiology, 166:427-442, 2005.

Cecchin et al, "Seizure lateralization in scalp EEG using Hjorth parameters", Clinical Neurophysiology, 121:290-300, 2010.

Gotman et al, "Graphic representation of the EEG during epileptic seizures", Electroencephalography and Clinical Neurophysiology, 87:206-214, 1993.

* cited by examiner

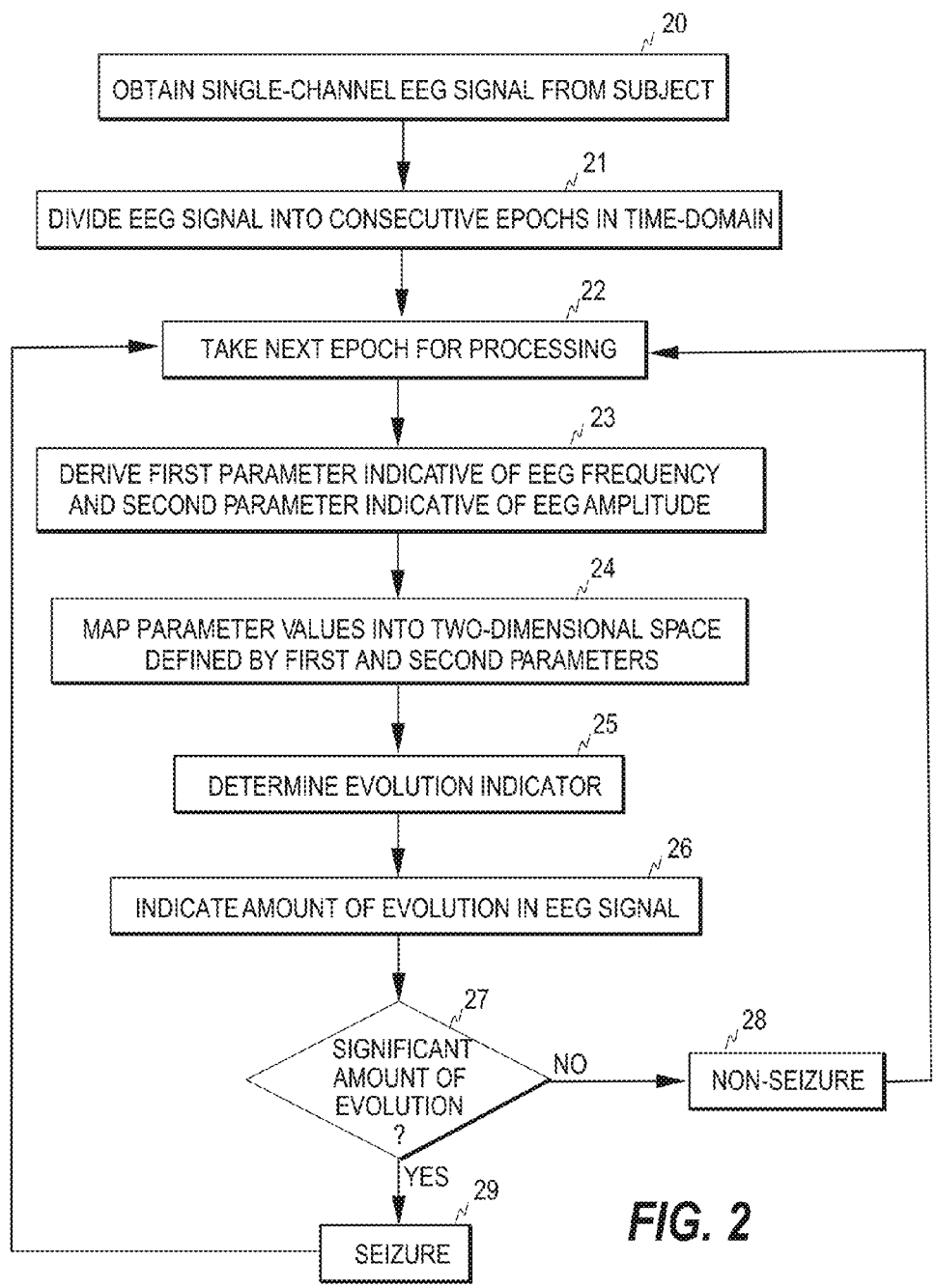
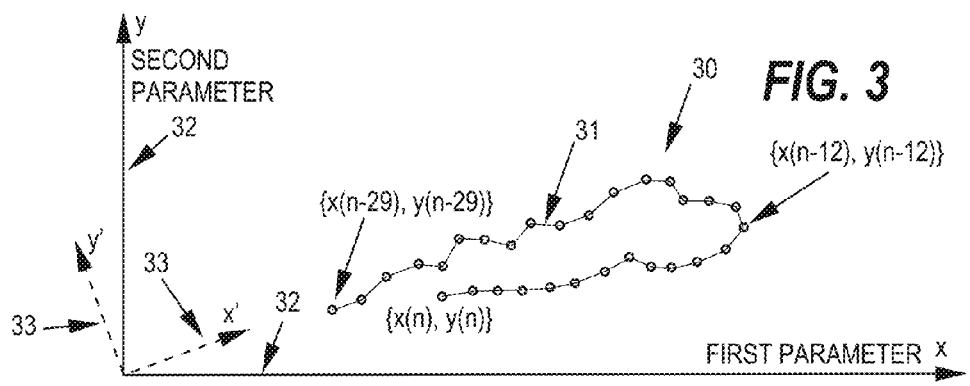
FIG. 3

METHOD AND APPARATUS FOR AUTOMATIC SEIZURE MONITORING

BACKGROUND OF THE INVENTION

This disclosure relates generally to monitoring of brain wave signals. More particularly, the present invention relates to a mechanism for monitoring evolution of brain wave signals and to automatic detection of seizure activity in the brain wave signals.

About 5% of the world's population experiences seizure activity some times during their life. When seizures occur repeatedly without external stimulation, a person suffers from epilepsy. About 0.5% of the entire population belongs to that core group, which makes epilepsy the most common neurological disorder. According to the current standardization, there are two main categories of seizures: generalized and partial seizures. Generalized seizures involve the whole brain, while partial seizures involve a restricted area of the brain. The main categories are further divided to several sub-categories, which describe the types of movements a person demonstrates and how the awareness and consciousness are affected during the seizure. In general, intense, paroxysmal, and involuntary muscle convulsions are called convulsions and are often related to seizures.

Electroencephalography (EEG) is a well-established method for assessing brain activity. Measurement electrodes are typically attached on the skin of the skull surface to record and analyze the weak biopotential signals generated in the pyramid cells of the cortex. Alternatively, electrodes may be attached invasively between the brain and skull, or inside the brain tissue. The EEG has been in wide use for decades in basic research of the neural systems of the brain as well as in the clinical diagnosis of various central nervous system diseases and disorders.

Documentation of behavior and EEG of epileptic patients offers important information for surgery planning, diagnosis and follow-up treatment of epilepsy. Because the seizures occur intermittently and unpredictably, long-term monitoring lasting for several days is typically used in order to catch enough information of the EEG and the behavioral manifestations related to seizures. These recordings are typically obtained in epilepsy monitoring units (EMUs) in hospitals where dedicated equipment and personnel are available for the purpose. Recent advances in the field of telemedicine and ambulatory recordings may, however, make home monitoring practicable for epileptic patients in the near future.

Long-term EEG recording produces a vast amount of EEG data, which is later reviewed by a certified specialist. In visual analysis, particular EEG waveform morphologies and dynamic patterns are searched for, which are known, based on experience, to correspond to seizures. Found morphologies and patterns are examined in detail for obtaining information about the type and origin of the seizure. As the visual analysis is based on pattern recognition conducted by a human observer, the analysis process contains certain limitations, such as subjectivity of seizure recognition and slowness of the analysis. Reviewing long-term EEG recordings may require several hours of work, and thus human brain may easily become exhausted and seizures may be missed, short ones in particular.

For aiding visual EEG review, automatic seizure detection algorithms have been developed since 1970's. However, because the EEG with seizure activity differs between patients, development of a universally functioning automatic detector is challenging. Recent advances in the field of automatic seizure detection are related to patient-specific seizure detectors, which are closing the performance gap between a human observer and computer based detectors. These detectors are semi-automatic; a human observer has to mark one seizure instance from the data before the detector can search for similar instances. Despite the recent advances in computing and the limitations of visual EEG review, it is still the state of the art of seizure detection.

Besides being important for diagnostic purposes, seizure detection has a vital role in care decisions aiming to prevent brain damage. If seizure activity does not relieve within a few minutes, the risk for irreversible brain damage increases drastically. Prolonged seizure activity is called status epilepticus (SE) and it is a major medical emergency. Patients suffering from SE are heavily treated in intensive care units (ICUs). Generalized SE leads to irreversible brain damage with lasting intellectual morbidity. Depending on the etiology, the mortality rate of generalized SE may be from 20 to 30%.

Within the last decade, the prevalence of seizures in ICU patients has been widely realized. It has been observed that even patients without a past history of epilepsy or any neurological disorder may express seizures in the ICU. The reason for these seizures may be related to critical illnesses, such as hypoxia, ischemia, intoxications, and metabolic abnormalities. Also, neurological pathologies like stroke, intracerebral hemorrhage, brain tumor, central nervous system infections, and traumatic brain injury increase the risk of seizures. What makes the seizure detection in this patient group especially challenging, is that a vast majority of the seizures are non-convulsive. That is, the patient does not exhibit intense movements during the seizure. According to the current knowledge, EEG is the only specific indicator of non-convulsive seizures. Actually, 18-34% of neurological intensive care patients suffering from unexplained depressed level of consciousness have been shown to have non-convulsive seizures and 10% of these patients are in non-convulsive status epilepticus (NCSE). According to the current understanding, non-convulsive seizures produce irreversible brain damage similarly as convulsive seizures do, and thus the medication is highly recommended for this patient group as well.

Seizure detection conducted for intensive care patients has set new requirements for automatic seizure detection algorithms. At the moment, these seizures are detected with the aid of continuous EEG monitoring and time-consuming visual EEG analysis. Seizures require acute treatment with anticonvulsants, and thus the delay related to visual reviewing is often detrimental to the patient. Consequently, there is an urgent need for automatic, on-line seizure detectors.

Commercially available automatic algorithms developed using data collected from the EMU's have not been evaluated properly for ICU patient population. In the EMUs, these detectors produce 0.6-2.4 false detections per hour. In the ICU environment, false positive rates are probable even higher, because the EEG of a neurologically ill ICU patient characteristically contains abnormal features closely resembling a seizure, such as triphasic waves and alpha coma. However, treating these abnormal EEG features with anticonvulsants may have detrimental effects to the patient. Therefore, reliable detection of seizure activity in the ICUs is especially important.

As described above, automatic seizure detection has remained a technical challenge for decades. New application areas, like ICU, and new knowledge of the criticality of non-convulsive seizures set new, more demanding criteria for the technical performance of automatic seizure detection. One signal feature that is observed by specialists in visual analysis is the time evolution of the seizure pattern. However, this criterion is practically omitted in known automated seizure detection algorithms. In their simplicity, known automatic EEG seizure detectors rely on signal characteristics like power and periodicity and are, thus, susceptible to false detections. Seizure evolution is characterized by sequential changes in the EEG, often visible in EEG frequency and amplitude. As commonly known, these changes are not specific for seizure activity only, because amplitude and frequency varies in neurologically healthy subjects as well, for example in relation to alterations in vigilance level.

BRIEF DESCRIPTION OF THE INVENTION

The above-mentioned problems are addressed herein which will be comprehended from the following specification. The specification describes a novel approach for quantifying time evolution of a brain wave signal, thus ultimately leading to improved accuracy of seizure detection. Here, evolution refers to the gradual development or process of developing that occurs in the brain wave signal and in signal parameters. In order to minimize false detections in automated seizure detection, the evolution of the brain wave signal is quantified through a path that sequential sets of parameters derived from the signal form in a parameter space. That is, signal evolution is quantified by quantifying the development that occurs in a path formed in a given time period in the parameter space. The process quantifies the series of events that take place in a given order and thus, differs from the statistics based methods, such as variance, which do not take into account the order of the sequential samples. One or more paths may be determined and the evolution quantifier of each path may serve as an evolution indicator that may be used in various ways to indicate the occurrence of seizure activity. The said ways depend, for example, on the number of paths determined. In a simple embodiment, one path may be formed and the length thereof may be used directly as the evolution indicator and thus also as an indicator of the occurrence of seizure activity, while in a multi-channel embodiment a plurality of paths may be determined and a final evolution indicator may be determined based on the plurality of paths. If the time period used for determining the path is constant, the path length corresponds to average speed in physical terms. Instead of the actual length, any parameter that is in some way indicative of the length may be used as the evolution indicator. For example, the path length may be converted to a suitable scale. In another embodiment, the evolution occurring in a path formed in a given time period may be determined by determining the derivatives of the lengths of the consecutive segments forming the path, i.e., instantaneous acceleration values, and determining the evolution indicator as the sum of the instantaneous acceleration values.

In an embodiment, a method for monitoring seizure activity in brain includes deriving at least one parameter set sequence from brain wave signal data obtained from a subject, wherein each parameter set sequence comprises sequential parameter sets and each parameter set comprises values for at least two signal parameters, the values being derived from the brain wave signal data. The method also includes determining a path formed by each of the at least one parameter set sequence in a parameter space defined by the at least two signal parameters, thereby to obtain at least one path. The method further includes calculating at least one evolution indicator, wherein each evolution indicator quantifies evolution occurred in respective path formed in a given time period in the parameter space and employing the at least one evolution indicator to produce an indication of seizure activity in the brain wave signal data.

In another embodiment, an apparatus for monitoring seizure activity in brain includes a parameter determination unit configured to derive at least one parameter set sequence from brain wave signal data obtained from a subject, wherein each parameter set sequence comprises sequential parameter sets and each parameter set comprises values for at least two signal parameters, and wherein the values are derived from the brain wave signal data. The apparatus also includes a path determination unit configured to determine a path formed by each of the at least one parameter set sequence in a parameter space defined by the at least two signal parameters, thereby to obtain at least one path. The apparatus further includes an indicator determination unit configured to calculate at least one evolution indicator, wherein each evolution indicator is indicative of quantitative evolution occurred in respective path formed in a given time period in the parameter space and an indication unit configured to employ the at least one evolution indicator, thereby to produce an indication of seizure activity in the brain wave signal data.

In a still further embodiment, a computer program product for monitoring seizure activity in brain comprises a first program product portion configured to derive at least one parameter set sequence from brain wave signal data obtained from a subject, wherein each parameter set sequence comprises sequential parameter sets and each parameter set comprises values for at least two signal parameters, and wherein the values are derived from the brain wave signal data. The computer program product also includes a second program product portion configured to determine a path formed by each of the at least one parameter set sequence in a parameter space defined by the at least two signal parameters, thereby to obtain at least one path. The computer program product further includes a third program product portion configured to calculate at least one evolution indicator, wherein each evolution indicator is indicative of quantitative evolution occurred in respective path formed in a given time period in the parameter space and a fourth program product portion configured to employ the at least one evolution indicator, thereby to produce an indication of seizure activity in the brain wave signal data.

Various other features, objects, and advantages of the invention will be made apparent to those skilled in the art from the following detailed description and accompanying drawings.

BRIEF DESCRIPTION OF THE DRAWINGS

FIG. 2 illustrates another embodiment of the method for monitoring seizure activity;

FIG. 3 illustrates the parameter space in case of the embodiment of FIG. 2;

DETAILED DESCRIPTION OF THE INVENTION

Figure 1:
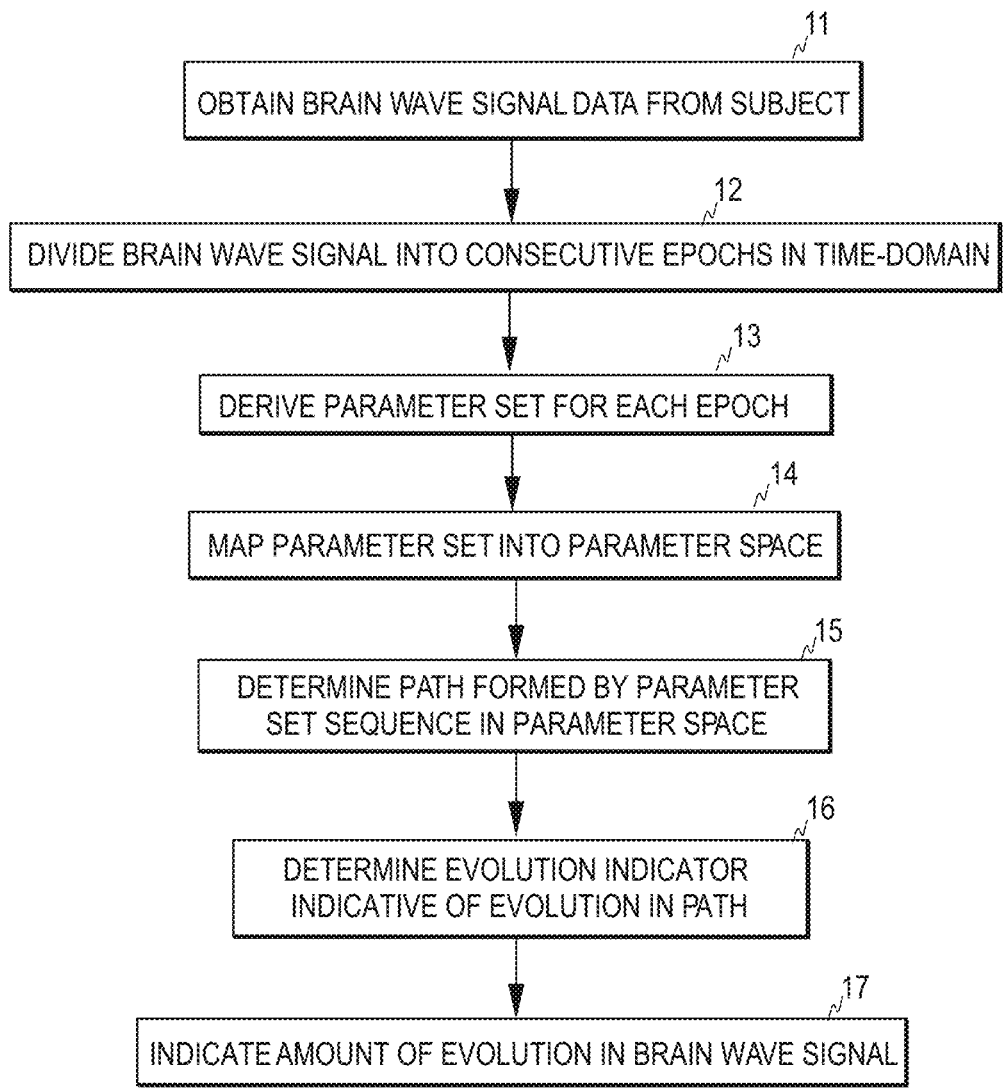
FIG. 1 illustrates one embodiment of a method for monitoring seizure activity.

FIG. 1 illustrates one embodiment of a method for monitoring a brain wave signal of a subject. The operations described relate to one measurement channel and similar operations may be applied to each measurement channel if multiple measurement channels are used. Multi-channel embodiments are discussed below in connection with FIG. 4.

As is common, the brain wave signal data obtained from the subject at step 11 is divided into consecutive segments or time windows, commonly termed epochs (step 12). The sequence of the epochs thus represents the brain wave signal data of the respective measurement channel and the signal may be processed epoch by epoch. The length of one epoch may vary, but may be, for example, one second. It is assumed here that the epochs are non-overlapping. Instead of the epochs, single sample values may be used, although the parameters to be derived will presumably be noisier in that case.

For each epoch, a parameter set comprising at least two parameters is derived from the signal data of the epoch (step 13). That is, in step 13 the brain wave signal is parameterized, thereby to obtain respective time sequences for at least two parameters that describe the signal. For example, parameters related to the amplitude and instantaneous frequency of the brain wave signal may be derived from the signal data. Alternatively, a first parameter related to the amplitude and a second parameter related to the spike rate may be derived. The determination of the parameters may include optional filtering, where the time-course of the parameters is smoothed and possible fluctuation removed. For example, median filtering of eleven sequential parameter values may be applied.

Next, the parameter values are mapped into a parameter space at step 14, thereby to track the sequential values in the parameter space. The parameter space here refers to a space whose N dimensions are respectively defined by the N parameters that are determined for each epoch (N≥2). That is, the concurrent parameter values define a point (or a subspace) in the parameter space. Typically, N equals two and the parameter space is thus a two-dimensional space, such as a plane or a coordinate system, in which one axis represents one parameter and the other axis the other parameter. When two parameters are used, the current state of the brain is represented by the point {x(n), y(n)} in the two-dimensional parameter space, where x(n) is the value of the first parameter, y(n) the value of the second parameter, and n the running number of the discrete sample points in the time series. The point {x(n), y(n)} is here termed a parameter point. That is, a parameter point is defined by the parameter set obtained for an epoch.

Evolution of the brain state is monitored by determining, at step 15, a path between the sequential parameter points in the parameter space. For example, the path may be determined from {x(n), y(n)} to {x(n+1), y(n+1)}, and from {x(n+1), y(n+1)} to {x(n+2), y(n+2)}, etc. In this context, the path is called an evolution path. The evolution path may be determined over a certain length of history, which may be tuned depending on the application. For example, in monitoring seizure evolution a suitable length of history may be from about 30 seconds to about 5 minutes. If the length of history is 30 seconds, for example, and consecutive, non-overlapping, one-second-long epochs are used, the evolution path is the line between points {x(n−29), y(n−29)}, {x(n−28), y(n−28)}, ... {x(n−2), y(n−2)}, {x(n−1), y(n−1)}, {x(n), y(n)}.

Several evolution paths may be derived from the same parameter point time series. For example, a first evolution path using a history of 30 seconds may be used for monitoring fast evolution and a second evolution path using a history of 3 minutes for monitoring slow evolution. Consequently, at each time instant, the evolution path covers a preceding time period of a predefined length and is indicative of the evolution of the parameters during that period.

An evolution indicator is then determined at step 16. The determined indicator may be indicative of the length of the evolution path. Using the above example, the path length may be calculated using the Pythagorean theorem: segment_length(n)=sqrt {{x(n)−x(n−1)}^2+{y(n)−y(n−1)}^2}; path_length(n)=sum{segment_length(n−29), segment_length(n−28), . . . , segment_length(n−2), segment_length(n−1), segment_length(n)}. That is, the length of each path segment is calculated, using the Pythagorean theorem, and the length of the evolution path is obtained as the sum of the segment lengths. Each path segment is determined by two sequential parameter points of the parameter space. The evolution indicator may be, for example, equal or directly proportional to the path length obtained, but may be any parameter that quantifies the evolution occurring in the path, i.e., in the series of the sequential parameter sets. Below, a parameter indicative of the length of a path that corresponds to a given time period is used as an example of the evolution indicator.

It is also possible that the path maintained is longer than the section over which the length is determined. Logically, the method thus comprises two steps for a sequence of parameter sets: the determination of the evolution path and the determination of the evolution indicator, such as the path length. At least the determination of the indicator is applied to a path formed in a given time period in the parameter space, and indicators may also be determined over several time periods, such as the 3 minute and 30 second periods mentioned above. Furthermore, in practice both the path and the evolution indicator (path length) may be updated epoch by epoch.

Long evolution paths indicate that substantial evolution has taken place in the brain wave signal. This is typically the case when seizure activity has occurred. Otherwise, there is typically much less evolution in the brain wave signal.

An indication of the amount of evolution in the brain wave signal is then given to the user at step 17. This indication may involve displaying the value of the evolution indicator determined in step 16, such as the path length or the path length value converted to a desired scale. If several measurement channels are used, the amount of evolution may be determined based on one or more channel-specific evolution indicators, as is discussed below.

It is obvious that even though FIG. 1 shows the acquisition and division of the brain wave signal as the first two steps, in online monitoring these steps are carried out continuously, and steps 13 to 17 are carried out for each epoch as a new epoch is obtained from step 12. The processing of the epochs may start when a given amount of history data has been collected. However, the method may also be used offline to monitor possible seizures in brain wave data acquired previously.

FIG. 2 illustrates another embodiment, in which seizures are detected. As above, it is assumed here that a sufficient amount of history data has already been collected, so that the evolution indicator (path length) may be determined. In this embodiment, a single channel EEG signal is obtained from a subject (step 20) and the signal is divided into consecutive epochs (step 21). Steps 21 and 22 are carried out continuously during the monitoring.

As a new epoch is obtained from the EEG signal, it is taken for processing (step 22). In this example, two parameters are derived from each new epoch; a first parameter indicative of EEG frequency and a second parameter indicative of EEG amplitude (step 23). The parameter values obtained are then mapped into a two-dimensional parameter space (step 24), such as an X-Y coordinate system where the x-axis represents the first parameter and the y-axis the second parameter (or vice versa). The evolution indicator is then determined at step 25 by determining the length of a path formed by a given number of preceding parameter points of the parameter space.

FIG. 3 illustrates an evolution path 30 comprising 30 parameter points {x(n−29), y(n−29)}, {x(n−28), y(n−28)}, ..., {x(n−1), y(n−1)}, {x(n), y(n)}, where x(n), y(n) is the most recent parameter point. The path length is the sum of the lengths of the segments 31, and the path length may again be used as the evolution indicator. In FIG. 3, the calculation of the path length is carried out with respect to the coordinate system 32 denoted with continuous axes. A transformed coordinate system 33 denoted with dashed axes is also shown in the figure. Coordinate transformations are discussed below in connection with embodiments employing orientation/direction based evolution indicators.

With reference to FIG. 2 again, an indication of the obtained amount of evolution may be given to the user at step 26. Further, the evolution indicator or path length may be compared with a predetermined or an adaptive seizure threshold value at step 27, thereby to make a decision on the presence of a seizure. If significant amount of evolution is detected at step 27, i.e., if the path length has reached the seizure threshold value, the process decides that the subject has a seizure (step 29) and an alarm may be raised to alert the nursing staff. If the path length does not reach the seizure threshold value, no seizure is detected (step 28). Having performed steps 23 to 28/29 for the current epoch, the process returns to step 22 to carry out the same steps for the next epoch of the EEG signal.

The number and types of the parameters to be derived epoch by epoch may depend on the application. For seizure detection in a two-dimensional space, one suitable parameter set may comprise a first parameter indicative of the instantaneous frequency and a second parameter indicative of the amplitude/power of a brain wave signal. These parameters may be estimated in various ways.

The frequency of a sinusoidal signal is a well-defined quantity. However, nonstationary signals, such as EEG, do not lend themselves well to decomposition into sinusoidal components. For such signals, the notion of frequency loses its effectiveness, and a parameter that accounts for the time-varying nature of the process needs to be used. Instantaneous frequency (IF) is a time-varying parameter, which defines the location of the signal's spectral peak as it varies with time. Physically, the said parameter is meaningful for single-component signals only. For multi-component signals, the notion of a single-valued instantaneous frequency becomes physically meaningless, although it may still characterize the frequency content of the signal under analysis. To overcome this limitation, a multi-component signal may be filtered to several adjacent frequency bands and the instantaneous frequency may be estimated within each band.

Hilbert transform is a traditional method for instantaneous frequency derivation. The Hilbert transform of a signal s(t) is obtained by:

$$H[s(t)] = p.v. \int_{-\infty}^{\infty} \frac{s(t-\tau)}{\pi\tau} d\tau,$$

where p.v. denotes the Cauchy principal value of the integral and r is the time lag. Signals s(t) and H[s(t)] are often said to be in quadrature, because in theory they are 90 degrees out of phase. However, in theory this is true only under certain conditions. Gabor's complex signal z(t) may be derived using the result of the Hilbert transform:

$$z(t) = s(t) + jH[s(t)] = a(t)e^{j\phi(t)}.$$

Using Gabor's complex signal z(t), instantaneous frequency IF may be derived by taking the derivative of the phase of signal z(t):

$$IF(t) = \frac{1}{2\pi} \frac{d}{dt}[\arg z(t)] = \frac{1}{2\pi} \frac{d\phi}{dt}$$

Mean IF value of the epoch may be used as a frequency related parameter.

Even moments of the signal are determined as:

$$\overline{\omega}_m = \int_{-\pi}^{\pi} \omega^m S(e^{j\omega}) d\omega,$$

where m is even and denotes the order of the moment, and $S(e^{j\omega})$ is the power spectral density of the signal. In this written application, the term signal moment is used in relation to the above equation, whereas the term spectral moment is sometimes used with the same meaning. As a person skilled in the art recognizes, the zeroth moment of a signal is the same as the total power of the signal.

Hjorth parameters or Hjorth slope descriptors have been widely used in EEG signal analysis since the 1970's. They are easy-to-calculate parameters for demonstrating the spectral properties of a signal. The first Hjorth parameter is activity. It corresponds to the zeroth moment of the same signal, i.e., to total power. The second Hjorth parameter is mobility, defined as the square root of the normalized second order signal moment:

$$\text{Mobility} = \sqrt{\frac{\overline{\omega}_2}{\overline{\omega}_0}}.$$

Mobility characterizes the dominant frequency of a signal. Estimation of the dominant frequency using the mobility equation often produces a similarly looking time-curve as the IF derivation via Hilbert transform. Yet, there is still one Hjorth parameter called complexity. Complexity characterizes half the bandwidth of the signal and it is determined as:

$$\text{Complexity} = \left| \sqrt{\frac{\overline{\omega}_4}{\overline{\omega}_2} - \frac{\overline{\omega}_2}{\overline{\omega}_0}} \right|.$$

Mobility and complexity have a physically meaningful relationship to the spectral landmarks, dominant frequency and respectively half the bandwidth, only in case of a unimodal power spectrum, i.e., in case of a signal with only one dominant frequency peak. In the case of multimodal signals this limitation may be avoided similarly as already described in connection with the Hilbert transform, i.e., by using a priori filtering, for example, thereby to divide the frequency range into several sub-bands.

Although the Hjorth parameters and the even signal moments are above determined via the power spectral density of the signal, they may also be estimated directly from the time-domain EEG signal. The first derivative $x^{(1)}$ and the second derivative $x^{(2)}$ of a signal may be approximated using two and three consecutive signal samples:

$x^{(1)}(n) = x(n) - x(n-1)$ $x^{(2)}(n) = x(n+1) - 2x(n) + x(n-1)$

Accordingly, estimates of the even signal moments may be determined using the following time domain average:

$$\hat{\omega}_m \approx \frac{2\pi}{N} \sum_{n=0}^{N-1} (x^{(m/2)}(n))^2, \quad m = 0, 2, 4, \ldots$$

Various other frequency estimates may also be produced through the consecutive time domain signal samples and derivatives, thereby to produce a univariate frequency parameter. For example, energy operators, such as a non-linear energy operator (NLEO) may be applied for that purpose. Nonlinear energy operator is defined as:

$\Psi_{NLEO}\{x(n)\} = x(n-l)x(n-p) - x(n-q)x(n-s)$, where the index values are selected so that $l+p=q+s$, and $|l-q|=|p-s|\neq 0$. The index values may be selected, for example as follows: $l=1$, $p=2$, $q=0$, and $s=3$. In EEG applications, the absolute value of NLEO is often preferred. The nonlinear energy operator, as defined above, is not a pure measure of frequency, since the changing signal amplitude affects it as well. To obtain a rough estimate of the signal frequency, the nonlinear energy operator may be divided by $x(n)^2$.

The number of times the signal changes sign during each epoch is a simple feature corresponding roughly to the dominant frequency of the signal. However, the main problem with the use of the feature as a frequency parameter is the sensitivity to noise. The rate of the zero crossings may, on the other hand, be used as a measure of the noisiness of the signal in some applications. Similarly as with the Hilbert transform and Hjorth parameters, a priori filtering may make the rate of the zero crossings less susceptible to noise.

Spectral edge frequencies denote the limit frequencies of the sub-bands containing given percentiles of the total power of the signal. For example, median frequency or 50% spectral edge frequency (SEF50%) denotes the limit frequency, which cuts the total power into two halves: 50% of the power resides below the SEF50% frequency and 50% above. Other commonly used SEF parameters are SEF90% and SEF95%, which indicate that 90% (or 95%) of the power of the signal is below the frequency concerned. Peak power frequency indicates the frequency with the highest power peak in the power spectral density. The mean frequency of the EEG may be calculated using the following equation:

$$MeanFreq = \frac{\sum_i f(i)S(i)}{\sum_i S(i)}$$

It should be noted that odd signal moments cannot be calculated using the power spectral density S, since it is an even function. Therefore, the numerator of the above equation is not the first moment of the signal. The odd moments of a signal may be derived from the power spectral density of Gabor's complex signal.

As described above, various techniques may be used to obtain a single parameter indicative of the current frequency content of the brain wave signal. The above frequency related parameters represent examples of the parameters that may be used as a frequency related parameter of the parameter set. However, any technique that produces a single parameter indicative of the frequency content of the brain wave signal data may be used in the parameterization phase of the signal.

The zeroth moment of the signal, i.e., the total power, is one alternative for the amplitude related parameter. As presented in the above equations, the total power may be derived either from power spectral density or directly from the time-domain signal. Another commonly used amplitude estimate is the root-mean-square (RMS) amplitude:

$$A_{RMS} = \sqrt{\frac{1}{N} \sum_{n=0}^{N-1} x(n)^2}.$$

Mean amplitude may be calculated as the average of the absolute signal sample values:

$$A_{mean} = \frac{1}{N} \sum_{n=0}^{N-1} |x(n)|.$$

Similarly, median amplitude may be derived from the absolute signal sample values. For peak-to-peak amplitude estimation, local minima and maxima are first searched for from the time-domain signal. After that, the differences of consecutive minima and maxima may be derived and used for the amplitude estimation. RMS, mean, and median peak-to-peak amplitudes may be derived similarly as described above, but by replacing the signal sample values with the difference values.

Various wave-decomposition methods have also been successfully employed in EEG signal analysis. These methods belong to the group of mimetic methods, since they often aim to mimic a human observer. In wave-decomposition methods, local minima and maxima may also be searched for, but more advanced logic and processing is often employed than in the simple peak-to-peak amplitude methods. Wave-decomposition methods may be fine-tuned to search for some predefined EEG patterns, such as EEG spikes. Using the output data of wave-decomposition, such as so-called half-waves, various amplitude and frequency estimates may be derived.

As in case of the frequency parameter, any appropriate technique may be used in the parameterization phase of the brain wave signal to produce a single parameter indicative of the current amplitude of the brain wave signal.

As discussed above, filtering prior to the generation of the parameters may lead to physically more meaningful parameters and improve the signal-to-noise ratio. Often, band-pass filtering improves the sensitivity and specificity of the parameters to track the EEG signal changes characteristic to seizure activity. EEG manifestations of seizure activity may be divided roughly into two categories; in the first category a significant amount of evolution takes place in the frequency and amplitude of the EEG within a short time period (from about 10 seconds to about 10 minutes), while in the second category spike activity consisting of periodical EEG spikes or sharp waves with a high repetition rate, typically at least three complexes per second, takes place. Frequency and amplitude evolution is often best visible in frequencies below about 20 Hz, whereas spike activity is best recognized in frequencies above 20 Hz. By proper selection of the cut-off frequencies of the in advance filtering, the method may be made more sensitive and specific to the seizure activity of interest.

When EEG is measured from the scalp of an adult, the EEG frequency range covers frequencies from 0 Hz to about 70 Hz. For monitoring evolutionary seizures, it is advantageous to remove at least part of the beta activity (13-30 Hz) and the entire gamma activity (30-70 Hz) of the EEG, thereby to improve the sensitivity and specificity of an automated seizure detector. Thus, a suitable cut-off frequency of a low-pass filter is between 12 and 20 Hz. Further, low frequencies may contain movement artifacts or other transients, or low-frequency fluctuation caused by perspiration or poor electrode contacts. Therefore, it is advantageous to use high-pass filtering with the cut-off frequency being somewhere between or around 1 and 2 Hz. After applying the above-described filters, the output data still contains the most relevant signal components characteristic to evolutionary seizures. As discussed above, the filtering may be carried out before the parameterization of the brain wave signal, and it may also be carried out before the division of the signal into consecutive epochs, i.e., before steps 12, 21, and 41.

The parameter space may also be expanded to dimensions higher than two, although the presentation and interpretation may become more complicated as the dimension of the parameter space increases. In case of a three-dimensional space, the third parameter may be, for example, spike rate, which defines how many spikes are detected in a predefined time window.

In one embodiment, the two-dimensional parameter space may be adaptive, i.e., the y-axis may represent one parameter, such as amplitude/power, but the parameter represented by the x-axis may vary. For example, x-axis may represent either instantaneous frequency or spike rate, depending on the type of seizure activity. Spike rate is a preferred parameter in case of detected spike activity, whereas instantaneous frequency is a preferred parameter for evolutionary seizures. However, many seizures are mixtures of these two categories. In other words, they have characteristics from both categories. Therefore, the process may determine a plurality of parameters from the signal data and monitor the evolution of each parameter. If a particular parameter shows significant evolution, one of the dimensions of the parameter space may be set to represent the said parameter. This may be applied to more than one parameter/dimension.

In another embodiment, the process may be tuned to be especially sensitive for the evolution in a particular area or towards to a particular direction of the parameter space. For example, in seizures the instantaneous frequency is typically higher than 2 Hz. Thus, the evolution indicator may be calculated only in the area located on the right side of the vertical line x=2 Hz. That is, the evolution path may be determined as above, but only the part of the path that is on the right side of the vertical line x=2 Hz may be taken into account when determining the evolution indicator.

Alternatively, the evolution indicator may be calculated towards a particular direction of the parameter space. For example, if the parameter space is defined by instantaneous frequency on the x-axis and amplitude on the y-axis, the evolution path during the partial seizures, i.e., seizures that affects a limited area of the brain only, often directs towards the upper-right corner of the parameter space. Various methods may be applied to produce orientation/direction based evolution indicators. For example, the coordinates (x,y) of a two-dimensional parameter space may be transformed to the new coordinates (x',y'), so that the x'-axis is formed by a straight line connecting the original origo and a desired point defined by the original coordinates, such as a point in the upper-right corner of the original (x,y) coordinate system. FIG. 3 shows an example, in which the original coordinate system 32 has been transformed to a new coordinate system 33 denoted with dashed axes. After the generation of the new coordinate system, evolution path length, or any other evolution path indicator may be calculated in the x'-direction. For example, if the same example as described above in connection with FIG. 1 is used, the segment and path lengths may be derived as follows: segment_length(n)=|x'(n)−x'(n−1)|; path_length(n)=sum{segment_length(n−29), segment_length(n−28), . . . , segment_length(n−2), segment_length(n−1), segment_length(n)}. If the segment length is calculated without the absolute value operation, path length values that are positive and large indicate developing seizure, whereas large negative values are indicative of a relieving seizure. Path length values close to zero are in turn indicative of a non-seizure period. In a general embodiment of the determination of the orientation/direction based evolution indicator, the path length indicator may be derived in N−1 dimensions, given that the original parameter space consists of N dimensions.

With reference to the above orientation/direction based embodiments, it is still to be noted here that within the parameter space one or more coordinate systems may thus be used to calculate the evolution indicator values. The coordinate system may be the original coordinate system or one or more coordinate systems may be transformed from the original coordinate system, thereby to obtain weighted evolution indicators. Yet, the parameter space remains common for all coordinate systems.

In embodiments comprising multiple signal channels temporal coherences of the parameters between the channels may also be examined. When a seizure takes place, the brain wave signals of different brain areas start to behave in a different manner, i.e., the seizure has a different effect in different brain areas. This is distinguishable especially when a partial seizure occurs.

Figure 4:
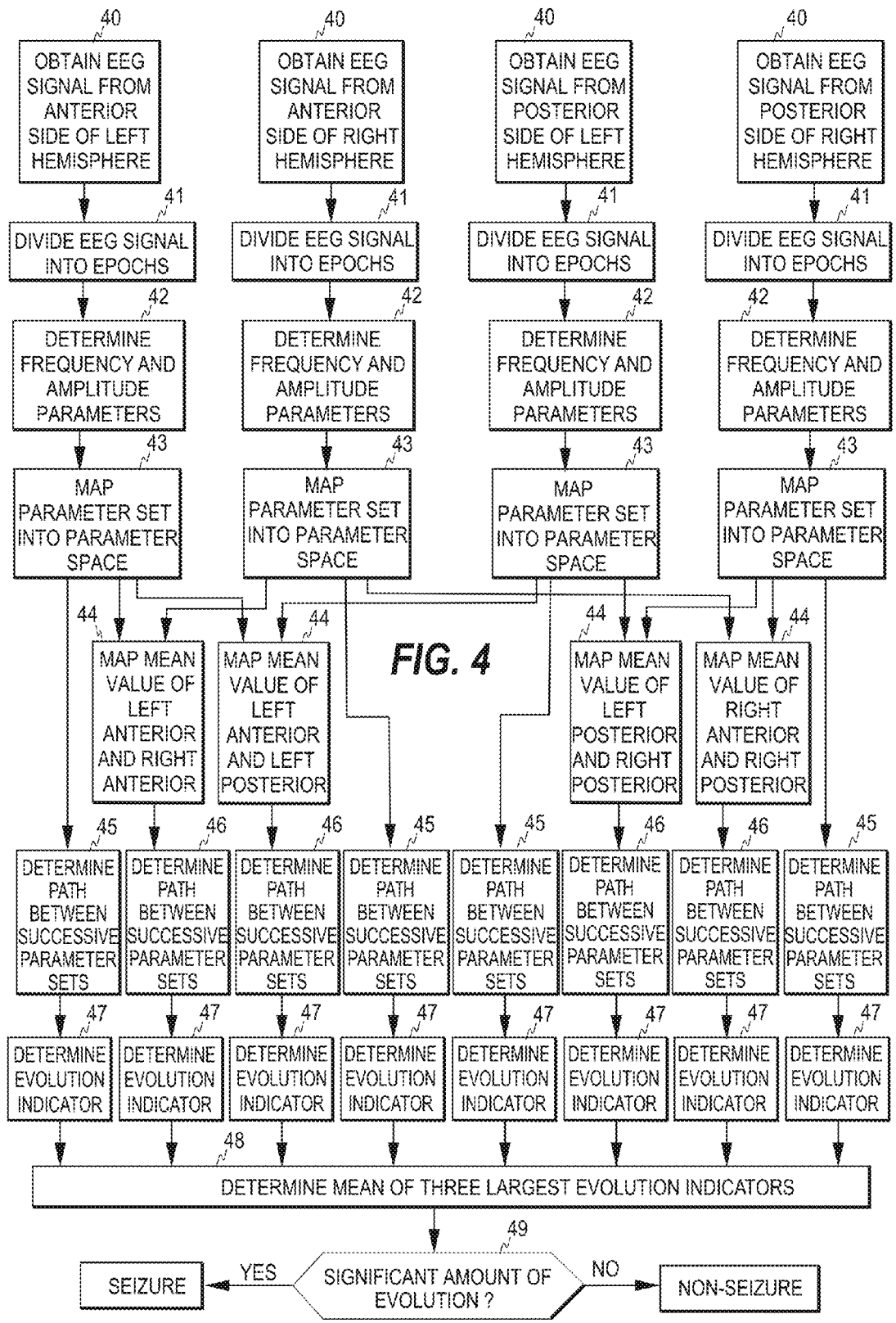
FIG. 4 illustrates a further embodiment of the method for monitoring seizure activity.

FIG. 4 illustrates one possible embodiment of a multi-channel monitoring mechanism. In this example, four-channel EEG signal data is acquired from the subject at steps 40; two channels from the left hemisphere and two channels from the right hemisphere. Two EEG signals are thus obtained from each hemisphere; the measurement site of the first one of the two EEG signals is closer to the frontal brain area, while the measurement site of the second one is farther from the frontal brain area, but closer to the occipital brain area. Furthermore, the measurement site of one of the said two signals may be closer to the temporal brain area than that of the other signal. In this way, all three dimensions of the brain may be utilized: cranial-caudal, anterior-posterior, and medial-lateral. It is advantageous that the electrodes are positioned in identical positions contra-laterally, i.e., that each electrode of the left hemisphere has a pair on the corresponding brain area of the right hemisphere. The signal of each channel is again divided into consecutive epochs (steps 41).

In the example of FIG. 4, two parameters are determined for each epoch of each channel; one indicative of the amplitude and the other indicative of the frequency of the respective signal (steps 42). The parameters of each channel are then mapped to the parameter space at steps 43 (as discussed above, it is assumed here that the parameter space is common for all channels). In addition to the four channel-specific parameter sets (each comprising the said two parameters), mean parameter sets {amplitude, frequency} between the channels of the same hemisphere and between the corresponding channels of opposite hemispheres are derived and mapped into the parameter space (steps 44). Consequently, four additional parameter sets are obtained for each epoch, each additional set comprising a mean value of the amplitude parameter and a mean value of the frequency parameter.

As a result, four channel-specific parameter sets and four additional parameter sets are obtained and thus totally eight evolution paths may be derived from the four EEG signal channels obtained from the subject; four channel-specific paths determined in steps 45 based on channel-specific parameters and four additional paths determined in steps 46 based on inter-channel mean values of the parameters. Eight separate path length based indicators are then determined in steps 47. The indicators derived from the data of two or more different channels are here termed additional evolution indicators, while the term evolution indicator may refer to a channel-specific indicator or to an additional evolution indicator.

When a seizure is detected, it is detectable on one or more of the EEG signal channels. That is, for the detection of a seizure it is enough to be able to detect the seizure on one of the EEG channels, since a seizure may occur locally in the brain. If a seizure is detectable only on one of the above four channels, three evolution paths are still lengthened: the path derived from the EEG channel where the seizure is detectable and the two other paths that are affected by the said EEG channel. An increase can thus be seen in three evolution indicators: in the evolution indicator derived from the said EEG channel and in the two additional evolution indicators on which the said channel affects. Thus, to detect seizures efficiently, the mean value of the three longest evolution paths may be used for detecting seizures. Consequently, once the eight path length based indicators have been determined in steps 47, three largest indicator values may be found out and the mean of the said three indicators may be determined in step 48. This value is then compared with a seizure threshold value at step 49, thereby to decide whether or not a seizure is present. The final evolution indicator may thus be obtained based on one or more evolution paths, cf. steps 25 and 48.

Compared to the single-channel embodiment of FIG. 2, the multi-channel embodiment of FIG. 4 offers improved perceptivity in seizure detection, since it is more efficient in detecting seizures confined to a limited area of the brain. In other multi-channel embodiments, it may not be necessary to use all channels for the determination of the evolution indicator, but the method may be applied to a subset of channels. Moreover, it may not be necessary to calculate paths based on inter-channel parameter values, but only channel-specific paths may be used. However, depending on the application it may also be possible that all evolution indicators are additional evolution indicators formed based on the brain wave data of two or more channels. If additional evolution indicators are determined based on one or more channel pairs or other channel combinations, the number of such additional indicators may vary. Furthermore, another aggregate value than the mean may be determined based on a channel pair or channel combination.

The parameters determined may also be provided with predefined weighting factors. For example, in the examples of FIGS. 5 and 6 the weighting factor is one for the frequency parameter of the x-axis, but $\log_{10}$ for the amplitude parameter of the y-axis. The usage of different weights for the parameters may improve the sensitivity and specificity of the seizure detection.

Figure 5:
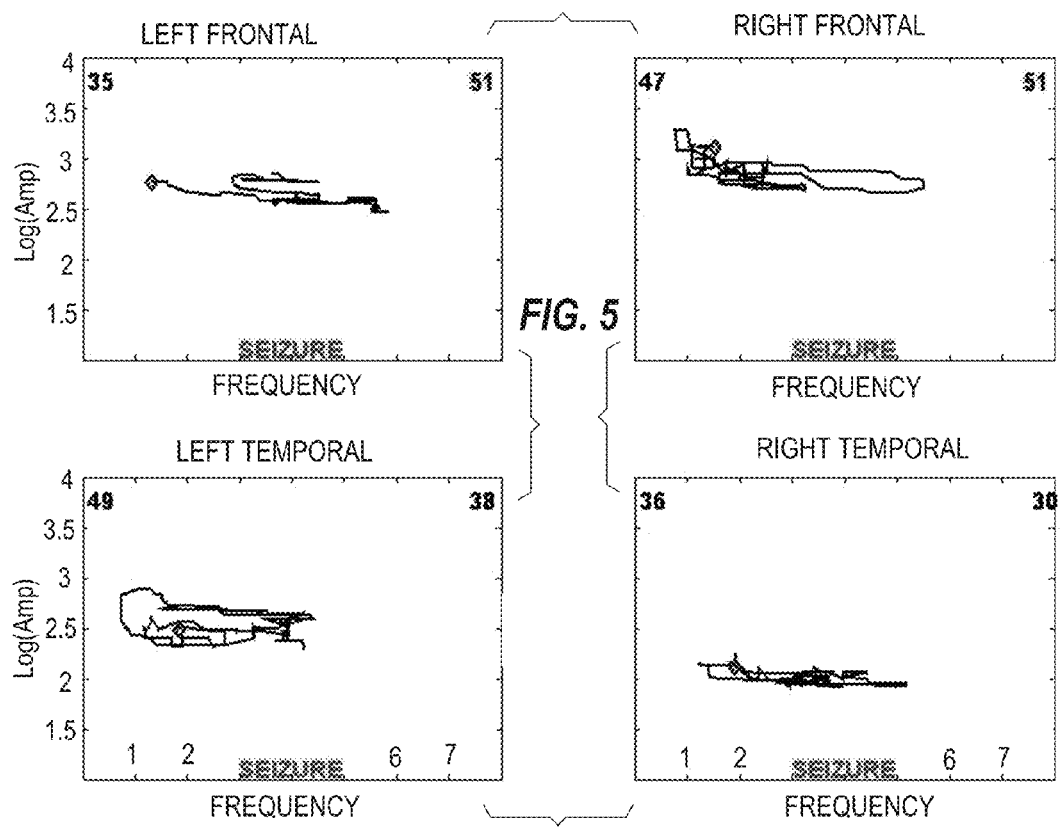
FIG. 5 illustrates an example the evolution paths of four different channels during a seizure period.

FIG. 5 illustrates an example of the evolution paths of four different channels obtained from a so-called sub-hairline EEG electrode montage during a seizure period. This snapshot presents a typical example of an evolutionary seizure; the frequency and amplitude evolve sequentially producing easily observable loops in the parameter space. The number on the top left corner of each graph presents the length of path formed in three minutes and the number on the top right corner the length of a path formed in forty seconds. The values are normalized to make them comparable.

Figure 6:
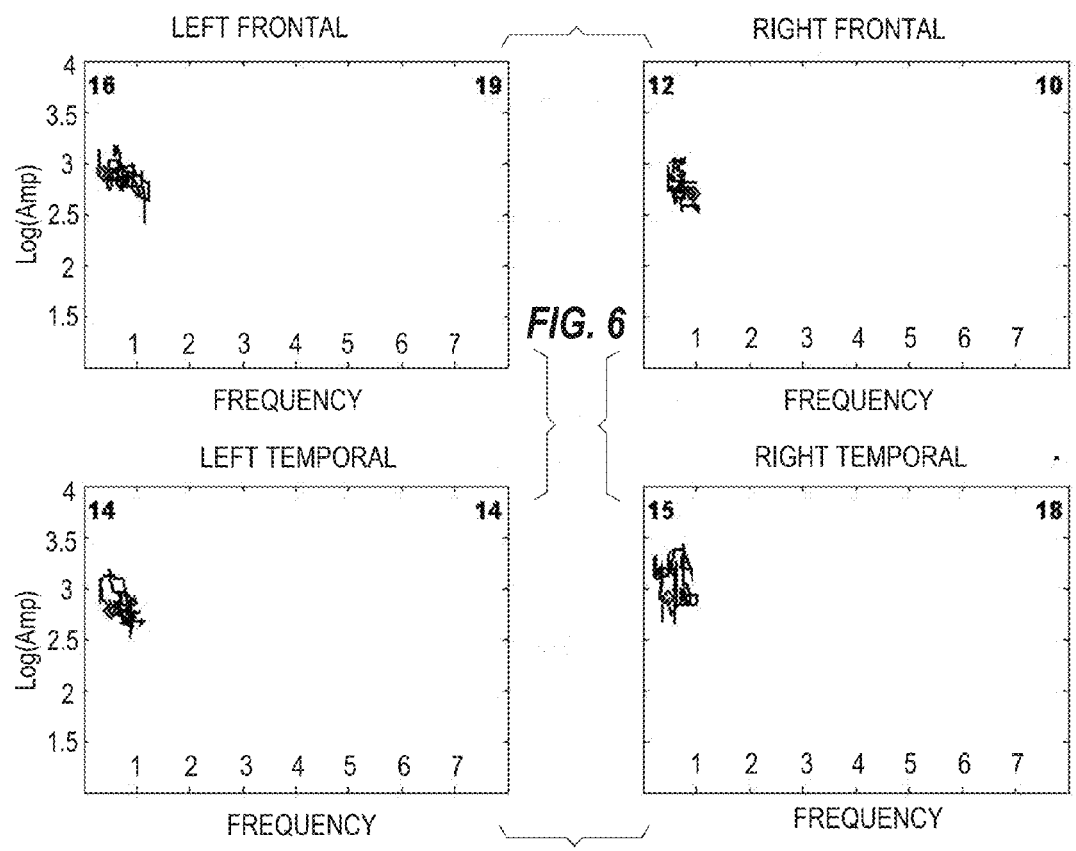
FIG. 6 illustrates an example of the evolution paths of four different channels during a non-seizure period.

FIG. 6 illustrates an example of the evolution paths of the same channels during a non-seizure period. In this snapshot, there is no significant evolution in any of the channels and the difference to the example of FIG. 5 is therefore remarkable.

In one embodiment, techniques like Self Organizing Map (SOM) may be used to map the parameters into the parameter space. In these embodiments, the evolution path may be determined in a two-dimensional plane, i.e., in a map, although the number of parameters is greater than two. This is because the technique provides an efficient way of visualizing parameter spaces having a dimension greater than two. The parameter space is now divided into several adjacent cells, each cell reserving a particular predefined small area in the two-dimensional plane. Furthermore, certain range of parameter values {x_low ... x_high, y_low ... y_high, z_low ... z_high, etc. ... } represents each cell. The cells representing similar type of brain activity are located close to each other in the two-dimensional plane, whereas the cells representing different types of activities are far from each other. The current state of the brain may be represented by the current active_cell(n) in the parameter space, and the next state may be represented by the active_cell(n+1). Again, the evolution path is the path connecting a given number of sequential active cells. Parameters like amplitude/power, instantaneous frequency, and spike rate may represent the cells. The use of SOM allows both seizure detection and identification of the seizure type, since the cells represent spiky seizures, which are on a map area different from the map area of the cells of non-spiky seizures.

Above, a parameter indicative of the path length is used as an example of the evolution indicator. However, any parameter may be used that quantifies the evolution occurring in the time series of the parameter set within a time period, i.e., in the path that corresponds to the time period. For example, the evolution indicator may represent the sum of the derivatives of the path segment lengths, i.e., the sum of the instantaneous acceleration values.

Figure 7:
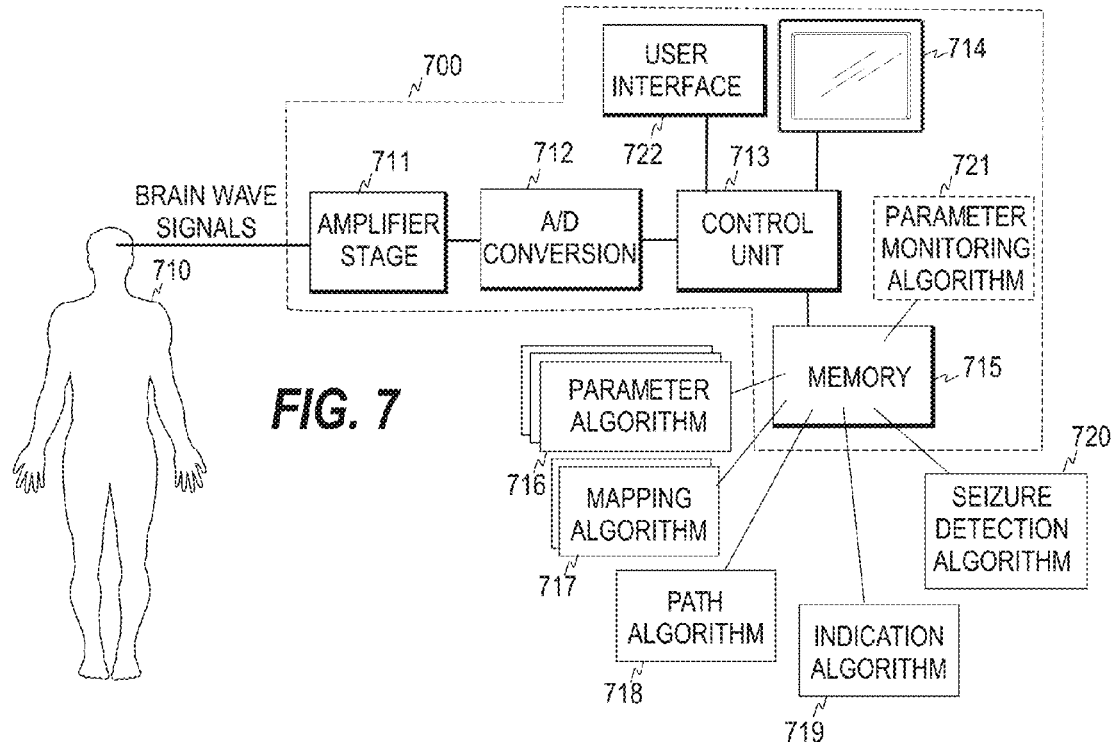
FIG. 7 illustrates an apparatus/system for monitoring seizure activity based on one or more brain wave signals.

FIG. 7 illustrates one embodiment of the apparatus or system for monitoring seizure activity. The brain wave data acquired from a subject/patient 710 is typically EEG signal data. In the case of a single or dual channel EEG measurement, the forehead of the patient is a preferred EEG measurement site due to the ease of use of the measurement and the reduced inconvenience caused to the patient. However, various electrode placement systems may be used, especially in multi-channel embodiments. One possible placement system is described in connection with FIG. 4.

The signals obtained from the EEG sensors are supplied to an amplifier stage 711, which amplifies the signals before they are sampled and converted into digitized format in an A/D converter 712. The digitized signals are then supplied to a control and processing unit 713 (including a microprocessor), which may then record the signals as an EEG time series and divide the signals into consecutive epochs.

The control and processing unit is provided with a memory or database unit 715 holding the digitized EEG signal data obtained from the sensors. Before the actual evaluation of the signal data, the control and processing unit may perform various pre-processing phases for improving the quality of the EEG signal data or the said phases may be carried out in separate elements located between the EEG sensors and the control and processing unit. The actual recording of the EEG signal data thus occurs in a conventional manner, i.e., the measurement device 700 including the above elements serves as a conventional EEG measurement device.

Additionally, the control and processing unit is provided with executable algorithms for monitoring seizure activity in the EEG channel data. For determining the parameters epoch by epoch for each channel, the control and processing unit uses one or more parameter determination algorithms 716 to derive the parameters from the signal data. The control and processing unit further uses one or more mapping algorithms 717 to map the parameter values into the parameter space, thereby to obtain at least one sequence of parameter points in the parameter space, and a path algorithm 718 configured to determine the parameter point path(s) and the respective evolution indicator(s). The control and processing unit is further provided with an indication algorithm 719 configured to produce an indication of seizure activity to the user. This may involve determining the final evolution indicator based on the channel-specific evaluation indicators, and possibly also the additional evaluation indicator(s), determined by the path algorithm.

If seizure detection is used, the control and processing unit may further be provided with a seizure detection algorithm 720 configured to make a decision on the presence of a seizure, when executed by the control and processing unit. If an adaptive parameter space is used, the control and processing unit may also be provided with a parameter monitoring algorithm 721, which, when executed by the control and processing unit, selects the parameters that define the parameter space.

The control and processing unit may display the results on the screen of a monitor 714 connected to the control and processing unit. This may be carried out in many ways using textual and/or graphical information about the amount of evolution and/or detected seizure. The information may be accompanied by visual and/or audible alarms, when a seizure is detected.

The system further includes a user interface 722 through which the user may control the operation of the system.

Figure 8:
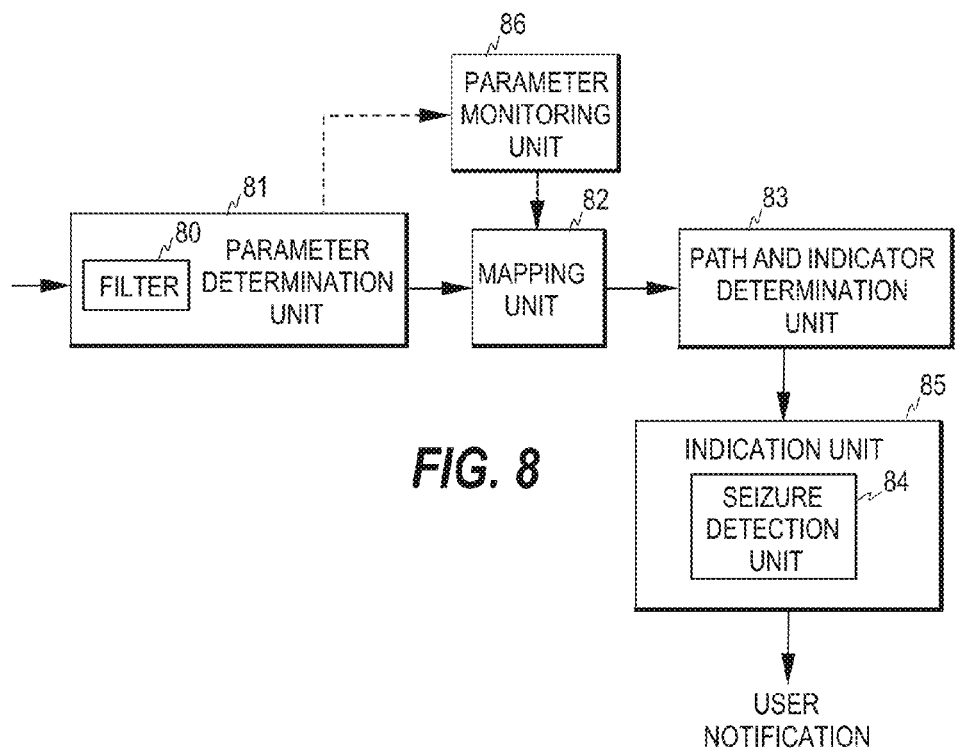
FIG. 8 illustrates the operational entities of the control and processing unit of the apparatus/system of FIG. 7.

As shown in FIG. 8, in terms of monitoring seizure activity the control and processing unit may thus include multiple operational entities: a parameter determination unit 81 configured to derive at least two parameters from each epoch of each channel used for the monitoring, a mapping unit 82 configured to map the parameters obtained from unit 81 to the parameter space, and a path and indicator determination unit 83 configured to determine the path(s) and the evolution indicator(s). The path and indicator determination unit 83 may thus be divided into separate sub-units; a first sub-unit (path determination unit) configured to determine the path(s) and a second sub-unit (indicator determination unit) configured to determine the evolution indicator(s). The parameter determination unit may be provided with a pre-filter 80 for removing gamma activity and part of the beta activity prior to the parameterization of the brain wave signal data.

The evolution indicator(s) is/are supplied as input data to an indication unit 85 configured to employ the input information, thereby to give an indication of seizure activity to the user. The indication unit may additionally include a seizure detection unit 84 configured to make decisions on the presence of a seizure. If an adaptive parameter space is used, the control and processing unit may further include a parameter monitoring unit 86 configured to select the parameters that define the parameter space.

It is to be noted that FIGS. 7 and 8 illustrate the division of the functionalities of the control and processing unit in logical sense and in view of evaluation of signal evolution. In a real apparatus the functionalities may be distributed in different ways between the elements or units of the apparatus. For example, the mapping functions and functions for determining the evolution indicators may be included in the same unit. Moreover, each unit may carry out its operations for one or more channels and the parameter unit may determine parameter aggregate values, such as mean values, for one or more channel pairs or channel combinations.

Furthermore, though one control and processing unit (data processing entity) may perform the calculations needed, the processing of the brain wave signal data may be distributed among different data processing entities within a distributed system or network, such as a hospital LAN (local area network). For example, a conventional measurement device may record the EEG signal data and an external computing entity, such as processor or server, may be responsible for seizure monitoring.

The brain wave signal data may be EEG signal data or magnetoencephalographic (MEG) signal data. MEG is indicative of the magnetic component of brain activity, i.e., it is the magnetic counterpart of EEG. The measurement device 700 may thus also serve as a conventional MEG measurement device, although a MEG measuring arrangement is far more expensive than an EEG measuring arrangement.

The software enabling a conventional EEG or MEG measurement device 700 to monitor/detect seizure waveforms may also be delivered separately to the measurement device, for example on a data carrier, such as a CD or a memory card, or through a telecommunications network. In other words, a conventional EEG or MEG measurement device may be upgraded by a plug-in unit that includes software enabling the measurement device to evaluate signal evolution and possibly also to detect seizures. The software module may comprise algorithms 716 to 719, and possibly also the detection algorithm 720. Thus, the software may also be used to analyze brain wave signal data offline. Should the conventional measurement device determine the parameters needed for the determination of the evolution indicator(s), it may be possible to omit the parameter algorithm 716. The software portion configured to derive the parameter set sequence(s) from the brain wave signal data may also include the above-described pre-filter configured to remove gamma activity and at least part of beta activity from the brain wave signal data prior to derivation of the parameter set sequence(s).

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for monitoring seizure activity in brain, the method comprising:
 acquiring brain wave signal data from a subject
 deriving at least one parameter set sequence from the brain wave signal data obtained from the subject, wherein each parameter set sequence comprises sequential parameter sets and each parameter set comprises values for two signal parameters comprising a first signal parameter and a second signal parameter, wherein the first signal parameter is a single value parameter indicative of the current frequency content of the brain wave signal data and the second signal parameter is a single value parameter indicative of the current amplitude of the brain wave signal data;
 determining a path formed by each of the at least one parameter set sequence in a parameter space wherein the parameter space is a two-dimensional coordinate system, and wherein a first axis represents values of the first parameter and a second axis represents values of the second parameter, thereby to obtain at least one path;

calculating at least one evolution indicator, wherein each evolution indicator quantifies evolution occurred in the respective path formed in a given time period in the parameter space; and employing the at least one evolution indicator to produce an indication of seizure activity in the brain wave signal data.

2. The method according to claim 1, wherein the acquiring includes acquiring a plurality of brain wave signal channels from the subject, in which the brain wave signal data belongs to the plurality of brain wave signal channels, the deriving includes deriving the parameter set sequence for each of the plurality of brain wave signal channels, thereby to obtain a corresponding plurality of parameter set sequences;

the determining includes determining a path for each of the plurality of parameter set sequences, thereby to obtain a corresponding plurality of paths;

the calculating includes calculating an evolution indicator for each of the plurality of paths, thereby to obtain a corresponding plurality of evolution indicators; and the employing includes employing the plurality of evolution indicators to produce an indication of seizure activity in the brain wave signal data.

3. The method according to claim 2, wherein the deriving further comprises deriving at least one additional parameter set sequence, wherein each additional parameter set sequence comprises sequential parameter sets, each parameter set comprising aggregate values for the two signal parameters derived from the corresponding areas of the opposite hemispheres or from the anterior and the posterior parts of the same hemisphere;

the determining further comprises determining a path formed by each of the at least one additional parameter set sequence in the parameter space, thereby to obtain at least one additional path;

the calculating further comprises calculating at least one additional evolution indicator, wherein each additional evolution indicator quantifies evolution occurred in respective additional path in the parameter space; and the employing further comprises (i) selecting n largest evolution indicators from an evolution indicator group comprising the at least one additional evolution indicator and the corresponding plurality of evolution indicators, where n is an integer greater than one, and (ii) producing a final evolution indicator based on the n largest evolution indicators, wherein the final evolution indicator is indicative of the seizure activity.

4. The method according to claim 1, wherein the employing includes making a decision on presence of a seizure.

5. The method according to claim 1, wherein the calculating includes calculating the at least one evolution indicator, in which the at least one evolution indicator is indicative of length of respective path formed in the given time period in the parameter space.

6. The method according to claim 1, wherein the first signal parameter is an instantaneous frequency derived via Hilbert transform, even signal moment of the order two or higher, nonlinear energy operator, rate of the zero crossings, median frequency, spectral edge frequency, peak power frequency, or mean frequency of the brain wave signal data.

7. The method according to claim 1, wherein the deriving includes low-pass filtering the brain wave signal data, thereby to remove gamma activity and at least part of beta activity from the brain wave signal, thereby producing a filtered brain wave signal containing frequencies below beta activity band, and wherein the low-pass filtering is applied prior to the deriving of the at least one parameter set sequence.

8. An apparatus for monitoring seizure activity in brain, the apparatus comprising:

a measurement unit configured to acquire brain wave signal data from a subject;

a parameter determination unit configured to receive brain wave signal data from the measurement unit and derive at least one parameter set sequence from brain wave signal data obtained from the subject, wherein each parameter set sequence comprises values for two signal parameters comprising a first signal parameter and a second signal parameter, wherein the first signal parameter is a single value parameter indicative of the current frequency content of the brain wave signal data and the second signal parameter is a single value parameter indicative of the current amplitude of the brain wave signal data;

a path determination unit configured to determine a path formed by each of the at least one parameter set sequence in a parameter space, wherein the parameter space is a two-dimensional coordinate system, and wherein a first axis represents values of the first parameter and a second axis represents values of the second parameter, thereby to obtain at least one path;

an indicator determination unit configured to calculate at least one evolution indicator, wherein each evolution indicator is indicative of quantitative evolution occurred in respective path formed in a given time period in the parameter space; and an indication unit configured to employ the at least one evolution indicator, thereby to produce an indication of seizure activity in the brain wave signal data.

9. The apparatus according to claim 8, wherein the measurement unit is configured to acquire a plurality of brain wave signal channels from the subject, in which the brain wave signal data belongs to the plurality of brain wave signal channels, the parameter determination unit is configured to derive the parameter set sequence for each of the plurality of brain wave signal channels, thereby to obtain a corresponding plurality of parameter set sequences;

the path determination unit is configured to determine the path for each of the plurality of parameter set sequences, thereby to obtain a corresponding plurality of paths;

the indicator determination unit is configured to calculate an evolution indicator for each of the plurality of paths, thereby to obtain a corresponding plurality of evolution indicators; and the indication unit is configured to employ the plurality of evolution indicators, thereby to produce an indication of seizure activity in the brain wave signal data.

10. The apparatus according to claim 9, wherein the parameter determination unit is further configured to determine at least one additional parameter set sequence, wherein each additional parameter set sequence comprises sequential parameter sets, each additional parameter set comprising aggregate values for the two signal parameters derived from the corresponding areas of the opposite hemispheres or from the anterior and the posterior parts of the same hemisphere;

the path determination unit is further configured to determine a path formed by each of the at least one additional parameter set sequence in the parameter space, thereby to obtain at least one additional path;

the indicator determination unit is further configured to calculate at least one additional evolution indicator, wherein each additional evolution indicator is indicative of quantitative evolution occurred in respective additional path formed in a given time period in the parameter space; and the indication unit is further configured to select n largest evolution indicators from an evolution indicator group comprising the at least one additional evolution indicator and the plurality of evolution indicators and to produce a final evolution indicator based on the n largest evolution indicators, wherein the final evolution indicator is indicative of the seizure activity and n is an integer greater than one.

11. The apparatus according to claim 8, wherein the indication unit is configured to make a decision on presence of a seizure.

12. The apparatus according to claim 8, wherein the at least one evolution indicator is indicative of length of respective path formed in the given time period in the parameter space.

13. The apparatus according to claim 8, wherein the parameter determination unit comprises a low-pass pre-filter configured to remove gamma activity and at least part of beta activity from the brain wave signal data, thereby producing filtered brain wave signal data containing frequencies below beta activity band.

14. The apparatus according to claim 8, wherein the first signal parameter is an instantaneous frequency derived via Hilbert transform, even signal moment of the order two or higher, nonlinear energy operator, rate of the zero crossings, median frequency, spectral edge frequency, peak power frequency, or mean frequency of the brain wave signal data.

* * * * *